United States Patent
Ebrahimi et al.

(10) Patent No.: US 11,839,729 B2
(45) Date of Patent: Dec. 12, 2023

(54) DILATION INSTRUMENT WITH MALLEABLE GUIDE AND DILATION CATHETER WITH INTEGRAL POSITION SENSOR

(71) Applicant: Acclarent, Inc., Irvine, CA (US)

(72) Inventors: Babak Ebrahimi, Irvine, CA (US); Ehsan Shameli, Irvine, CA (US); George L. Matlock, Pleasanton, CA (US); John H. Thinnes, Jr., Mission Viejo, CA (US); Fatemeh Akbarian, Rancho Palos Verdes, CA (US)

(73) Assignee: Acclarent, Inc., Irvine, CA (US)

( * ) Notice: Subject to any disclaimer, the term of this patent is extended or adjusted under 35 U.S.C. 154(b) by 957 days.

(21) Appl. No.: 16/532,671

(22) Filed: Aug. 6, 2019

(65) Prior Publication Data
US 2020/0108237 A1    Apr. 9, 2020

Related U.S. Application Data

(60) Provisional application No. 62/741,614, filed on Oct. 5, 2018.

(51) Int. Cl.
| | |
|---|---|
| *A61M 29/02* | (2006.01) |
| *A61B 17/24* | (2006.01) |
| *A61M 25/01* | (2006.01) |
| *A61B 34/20* | (2016.01) |

(Continued)

(52) U.S. Cl.
CPC .............. *A61M 29/02* (2013.01); *A61B 17/24* (2013.01); *A61B 34/20* (2016.02); *A61F 11/20* (2022.01); *A61M 25/0105* (2013.01); *A61B 2034/2057* (2016.02); *A61M 25/1025* (2013.01);

(Continued)

(58) Field of Classification Search
CPC ........ A61B 17/12022; A61B 17/12104; A61B 17/12136; A61B 17/24; A61B 34/20; A61B 2034/2051; A61B 2034/2057; A61F 11/20; A61M 25/01; A61M 25/0105; A61M 25/0662; A61M 25/10; A61M 25/1025;

(Continued)

(56) References Cited

U.S. PATENT DOCUMENTS

| | | |
|---|---|---|
| 7,720,521 B2 | 5/2010 | Chang et al. |
| 9,962,530 B2 | 5/2018 | Johnson et al. |
| 10,561,370 B2 | 2/2020 | Salazar et al. |

(Continued)

FOREIGN PATENT DOCUMENTS

WO    WO 2011/140535 A1    11/2011

OTHER PUBLICATIONS

International Search Report and Written Opinion dated Jan. 13, 2020 for International Application No. PCT/IB2019/058302, 10 pages.

*Primary Examiner* — Robert A Lynch
(74) *Attorney, Agent, or Firm* — Frost Brown Todd LLP

(57) ABSTRACT

An apparatus includes a handle assembly, a guide tube, and a dilation catheter. The guide tube extends distally from the handle assembly. At least a distal portion of the guide tube is malleable. The dilation catheter is slidably positioned in the guide tube. The dilation catheter includes a distal end, a dilator, and a position sensor. The position sensor is configured to generate a signal indicating a position of the position sensor in three-dimensional space. The dilation catheter is configured to translate relative to the guide tube.

4 Claims, 7 Drawing Sheets

(51) Int. Cl.
*A61F 11/20* (2022.01)
*A61M 25/10* (2013.01)
(52) U.S. Cl.
CPC ............. *A61M 2029/025* (2013.01); *A61M 2210/0675* (2013.01)
(58) Field of Classification Search
CPC .......... A61M 2025/0681; A61M 29/00; A61M 29/02; A61M 2029/025; A61M 2210/0675
See application file for complete search history.

(56) References Cited

U.S. PATENT DOCUMENTS

| | | | |
|---|---|---|---|
| 2009/0149807 A1* | 6/2009 | Bonnette | A61M 25/10182 604/98.01 |
| 2010/0099946 A1* | 4/2010 | Jenkins | A61B 1/0014 606/199 |
| 2010/0274188 A1 | 10/2010 | Chang et al. | |
| 2011/0004057 A1 | 1/2011 | Goldfarb et al. | |
| 2012/0071857 A1 | 3/2012 | Goldfarb et al. | |
| 2013/0274715 A1 | 10/2013 | Chan et al. | |
| 2014/0180328 A1 | 6/2014 | Vaccaro et al. | |
| 2014/0364725 A1 | 12/2014 | Makower | |
| 2016/0008083 A1 | 1/2016 | Kesten et al. | |
| 2016/0270863 A1* | 9/2016 | Makower | A61M 29/02 |
| 2016/0310042 A1 | 10/2016 | Kesten et al. | |
| 2016/0346515 A1* | 12/2016 | Buller | A61M 25/09041 |
| 2017/0120020 A1 | 5/2017 | Lin et al. | |
| 2018/0264237 A1 | 9/2018 | Palushi et al. | |
| 2019/0125375 A1 | 5/2019 | Palushi et al. | |
| 2019/0160268 A1 | 5/2019 | Ngo-Chu et al. | |
| 2019/0167351 A1 | 6/2019 | Salazar et al. | |

* cited by examiner

DILATION INSTRUMENT WITH MALLEABLE GUIDE AND DILATION CATHETER WITH INTEGRAL POSITION SENSOR

PRIORITY

This application claims priority to U.S. Provisional Pat. App. No. 62/741,614, entitled "Dilation Instrument with Malleable Guide and Dilation Catheter with Integral Position Sensor," filed Oct. 5, 2018, the disclosure of which is incorporated by reference herein.

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guide wire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, now abandoned, the disclosure of which is incorporated by reference herein. An example of such a system is the Relieva® Spin Balloon Sinuplasty™ System by Acclarent, Inc. of Irvine, Calif.

In the context of Eustachian tube dilation, a dilation catheter or other dilation instrument may be inserted into the Eustachian tube and then be inflated or otherwise expanded to thereby dilate the Eustachian tube. The dilated Eustachian tube may provide improved ventilation from the nasopharynx to the middle ear and further provide improved drainage from the middle ear to the nasopharynx. Methods and devices for dilating the Eustachian tube are disclosed in U.S. Patent Pub. No. 2010/0274188, entitled "Method and System for Treating Target Tissue within the ET," published on Oct. 28, 2010, now abandoned, the disclosure of which is incorporated by reference herein; and U.S. Patent Pub. No. 2013/0274715, entitled "Method and System for Eustachian Tube Dilation," published on Oct. 17, 2013, now abandoned, the disclosure of which is incorporated by reference herein. An example of such a system is the Aera® Eustachian Tube Balloon Dilation System by Acclarent, Inc. of Irvine, Calif.

Image-guided surgery (IGS) is a technique where a computer is used to obtain a real-time correlation of the location of an instrument that has been inserted into a patient's body to a set of preoperatively obtained images (e.g., a CT or MRI scan, 3-D map, etc.), such that the computer system may superimpose the current location of the instrument on the preoperatively obtained images. An example of an electromagnetic IGS navigation systems that may be used in IGS procedures is the CARTO® 3 System by Biosense-Webster, Inc., of Irvine, Calif. In some IGS procedures, a digital tomographic scan (e.g., CT or MM, 3-D map, etc.) of the operative field is obtained prior to surgery. A specially programmed computer is then used to convert the digital tomographic scan data into a digital map. During surgery, special instruments having sensors (e.g., electromagnetic coils that emit electromagnetic fields and/or are responsive to externally generated electromagnetic fields) are used to perform the procedure while the sensors send data to the computer indicating the current position of each surgical instrument. The computer correlates the data it receives from the sensors with the digital map that was created from the preoperative tomographic scan. The tomographic scan images are displayed on a video monitor along with an indicator (e.g., crosshairs or an illuminated dot, etc.) showing the real-time position of each surgical instrument relative to the anatomical structures shown in the scan images. The surgeon is thus able to know the precise position of each sensor-equipped instrument by viewing the video monitor even if the surgeon is unable to directly visualize the instrument itself at its current location within the body.

While several systems and methods have been made and used in surgical procedures, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

Figure 1:
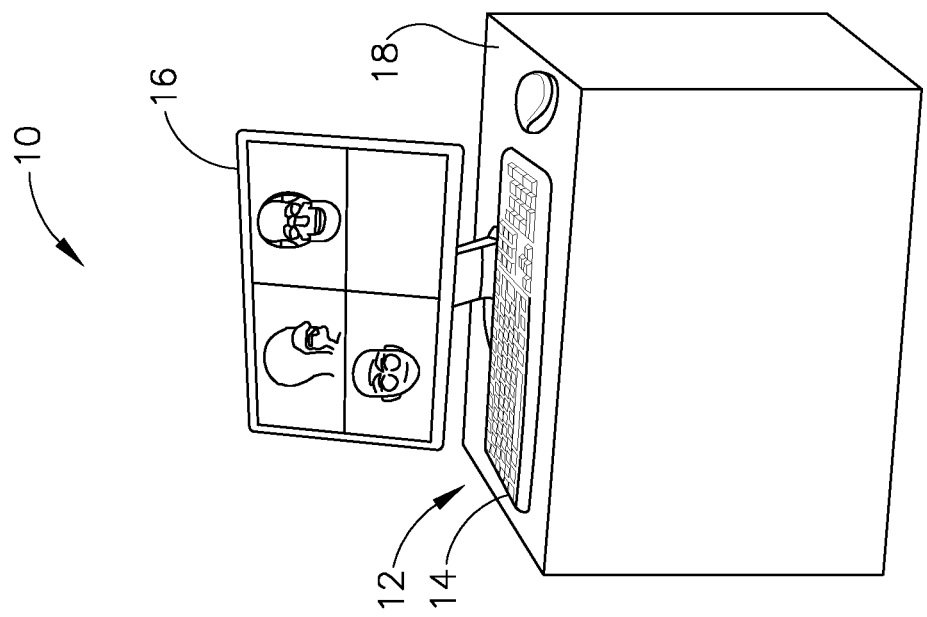
FIG. 1 depicts a schematic view of an exemplary surgery navigation system being used on a patient seated in an exemplary medical procedure chair.
Figure 1:
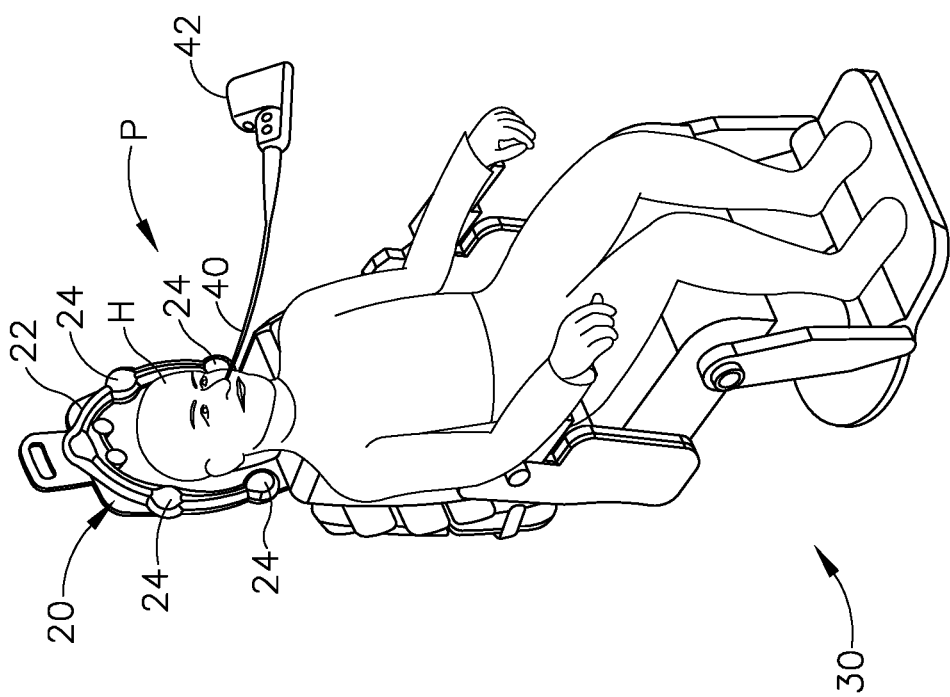

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

I. EXEMPLARY IMAGE GUIDED SURGERY NAVIGATION SYSTEM

When performing a medical procedure within a head (H) of a patient (P), it may be desirable to have information regarding the position of an instrument within the head (H) of the patient (P), particularly when the instrument is in a location where it is difficult or impossible to obtain an endoscopic view of a working element of the instrument within the head (H) of the patient (P). FIG. 1 shows an exemplary IGS navigation system (10) enabling an ENT procedure to be performed using image guidance. In addition to or in lieu of having the components and operability described herein IGS navigation system (10) may be constructed and operable in accordance with at least some of the teachings of U.S. Pat. No. 7,720,521, entitled "Methods and Devices for Performing Procedures within the Ear, Nose, Throat and Paranasal Sinuses," issued May 18, 2010, the disclosure of which is incorporated by reference herein; and U.S. Pat. Pub. No. 2014/0364725, entitled "Systems and Methods for Performing Image Guided Procedures within the Ear, Nose, Throat and Paranasal Sinuses," published Dec. 11, 2014, now abandoned, the disclosure of which is incorporated by reference herein.

IGS navigation system (10) of the present example comprises a field generator assembly (20), which comprises set of magnetic field generators (24) that are integrated into a horseshoe-shaped frame (22). Field generators (24) are operable to generate alternating magnetic fields of different frequencies around the head (H) of the patient (P). A navigation guidewire (40) is inserted into the head (H) of the patient (P) in this example. Navigation guidewire (40) may be a standalone device or may be positioned on an end effector or other location of a medical instrument such as a surgical cutting instrument or dilation instrument. In the present example, frame (22) is mounted to a chair (30), with the patient (P) being seated in the chair (30) such that frame (22) is located adjacent to the head (H) of the patient (P). By way of example only, chair (30) and/or field generator assembly (20) may be configured and operable in accordance with at least some of the teachings of U.S. patent application Ser. No. 15/933,737, entitled "Apparatus to Secure Field Generating Device to Chair," filed Mar. 23, 2018, issued as U.S. Pat. No. 10,561,370 on Feb. 18, 2020, the disclosure of which is incorporated by reference herein.

IGS navigation system (10) of the present example further comprises a processor (12), which controls field generators (24) and other elements of IGS navigation system (10). For instance, processor (12) is operable to drive field generators (24) to generate alternating electromagnetic fields; and process signals from navigation guidewire (40) to determine the location of a sensor in navigation guidewire (40) within the head (H) of the patient (P). Processor (12) comprises a processing unit communicating with one or more memories. Processor (12) of the present example is mounted in a console (18), which comprises operating controls (14) that include a keypad and/or a pointing device such as a mouse or trackball. A physician uses operating controls (14) to interact with processor (12) while performing the surgical procedure.

Navigation guidewire (40) includes a sensor (not shown) that is responsive to positioning within the alternating magnetic fields generated by field generators (24). A coupling unit (42) is secured to the proximal end of navigation guidewire (40) and is configured to provide communication of data and other signals between console (18) and navigation guidewire (40). Coupling unit (42) may provide wired or wireless communication of data and other signals.

In the present example, the sensor of navigation guidewire (40) comprises at least one coil at the distal end of navigation guidewire (40). When such a coil is positioned within an alternating electromagnetic field generated by field generators (24), the alternating magnetic field may generate electrical current in the coil, and this electrical current may be communicated along the electrical conduit(s) in navigation guidewire (40) and further to processor (12) via coupling unit (42). This phenomenon may enable IGS navigation system (10) to determine the location of the distal end of navigation guidewire (40) or other medical instrument (e.g., dilation instrument, surgical cutting instrument, etc.) within a three-dimensional space (i.e., within the head (H) of the patient (P), etc.). To accomplish this, processor (12) executes an algorithm to calculate location coordinates of the distal end of navigation guidewire (40) from the position related signals of the coil(s) in navigation guidewire (40). While the position sensor is located in guidewire (40) in this example, such a position sensor may be integrated into various other kinds of instruments, including those described in greater detail below.

Processor (12) uses software stored in a memory of processor (12) to calibrate and operate IGS navigation system (10). Such operation includes driving field generators (24), processing data from navigation guidewire (40), processing data from operating controls (14), and driving display screen (16). In some implementations, operation may also include monitoring and enforcement of one or more safety features or functions of IGS navigation system (10). Processor (12) is further operable to provide video in real time via display screen (16), showing the position of the distal end of navigation guidewire (40) in relation to a video camera image of the patient's head (H), a CT scan image of the patient's head (H), and/or a computer generated three-dimensional model of the anatomy within and adjacent to the patient's nasal cavity. Display screen (16) may display such images simultaneously and/or superimposed on each other during the surgical procedure. Such displayed images may also include graphical representations of instruments that are inserted in the patient's head (H), such as navigation guidewire (40), such that the operator may view the virtual rendering of the instrument at its actual location in real time. By way of example only, display screen (16) may provide images in accordance with at least some of the teachings of U.S. Pub. No. 2016/0008083, entitled "Guidewire Navigation for Sinuplasty," published Jan. 14, 2016, issued as U.S. Pat. No. 10,463,242 on Nov. 5, 2019, the disclosure of which is incorporated by reference herein. In the event that the operator is also using an endoscope, the endoscopic image may also be provided on display screen (16).

The images provided through display screen (16) may help guide the operator in maneuvering and otherwise manipulating instruments within the patient's head (H) when such instruments incorporate navigation guidewire (40). It should also be understood that other components of a surgical instrument and other kinds of surgical instruments, as described below, may incorporate a sensor like the sensor of navigation guidewire (40).

II. EXEMPLARY DILATION INSTRUMENT WITH MALLEABLE GUIDE AND DILATION CATHETER WITH INTEGRAL SENSOR

As noted above, it may be desirable to use an instrument to dilate one or more anatomical passageways within a head of a patient, including but not limited to a Eustachian tube, an ostium of a paranasal sinus, or other passageways associated with drainage of a paranasal sinus. Each anatomical passageway may require an entry angle that is uniquely associated with that particular anatomical passageway. For instance, entry of a dilation catheter into a maxillary sinus ostium may require an angle of entry that differs from the angle of entry required for entry of a dilation catheter into a frontal recess of a frontal sinus. It may therefore be desirable to provide an instrument guide feature that is malleable, thereby enabling the operator to adjust the dilation instrument based on the needs at hand. Malleability of an instrument guide feature may also allow the operator to dilate different passageways at different entry angles within the same medical procedure, such that the operator may bend the guide feature between dilations to achieve different exit angles. Examples of dilation instruments with malleable guide features are disclosed in U.S. Pub. No. 2012/0071857, entitled "Methods and Apparatus for Treating Disorders of the Sinuses," published Mar. 22, 2012, now abandoned, the disclosure of which is incorporated by reference herein; U.S. Pub. No. 2017/0120020, entitled "Apparatus for Bending Malleable Guide of Surgical Instrument," published May 4, 2017, issued as U.S. Pat. No. 10,137,286 on Nov. 27, 2018, the disclosure of which is incorporated by reference herein; and U.S. patent application Ser. No. 15/822,489, entitled "Guide Catheter for Dilation System," filed Nov. 27, 2017, now abandoned, the disclosure of which is incorporated by reference herein.

In addition to providing malleability in a guide feature of a dilation instrument, it may also be desirable to incorporate one or more position sensors into the dilation instrument, to provide compatibility with IGS navigation system (10). As noted above, this may be accomplished by incorporating a position sensor in a guidewire (40) that is used with the dilation instrument. In some instances, it may be desirable to use a dilation instrument without using a guidewire (40). In some such instances, a position sensor may be integrated into some other component of the dilation instrument, such as a dilation catheter. Examples of dilation catheters that incorporate a position sensor are described in U.S. patent application Ser. No. 15/797,049, entitled "Dilation Catheter with Navigation Sensor and Vent Passageway in Tip," filed Oct. 30, 2017, issued as U.S. Pat. No. 10,736,647 on Aug. 11, 2020, the disclosure of which is incorporated by reference herein; and U.S. patent application Ser. No. 15/830, 205, entitled "Dilation Instrument with Navigation and Distally Located Force Sensor," filed Dec. 4, 2017, issued as U.S. Pat. No. 10,864,046 on Dec. 15, 2020, the disclosure of which is incorporated by reference herein.

It may further be desirable to provide a dilation instrument that includes both a malleable guide feature and a position sensor that is integral with a dilation catheter, without requiring an additional guidewire. The malleability and position sensing may provide the benefits noted above; while omission of a guidewire may reduce the cost and complexity of the instrument. An example of such an instrument is described in greater detail below.

Figure 2:
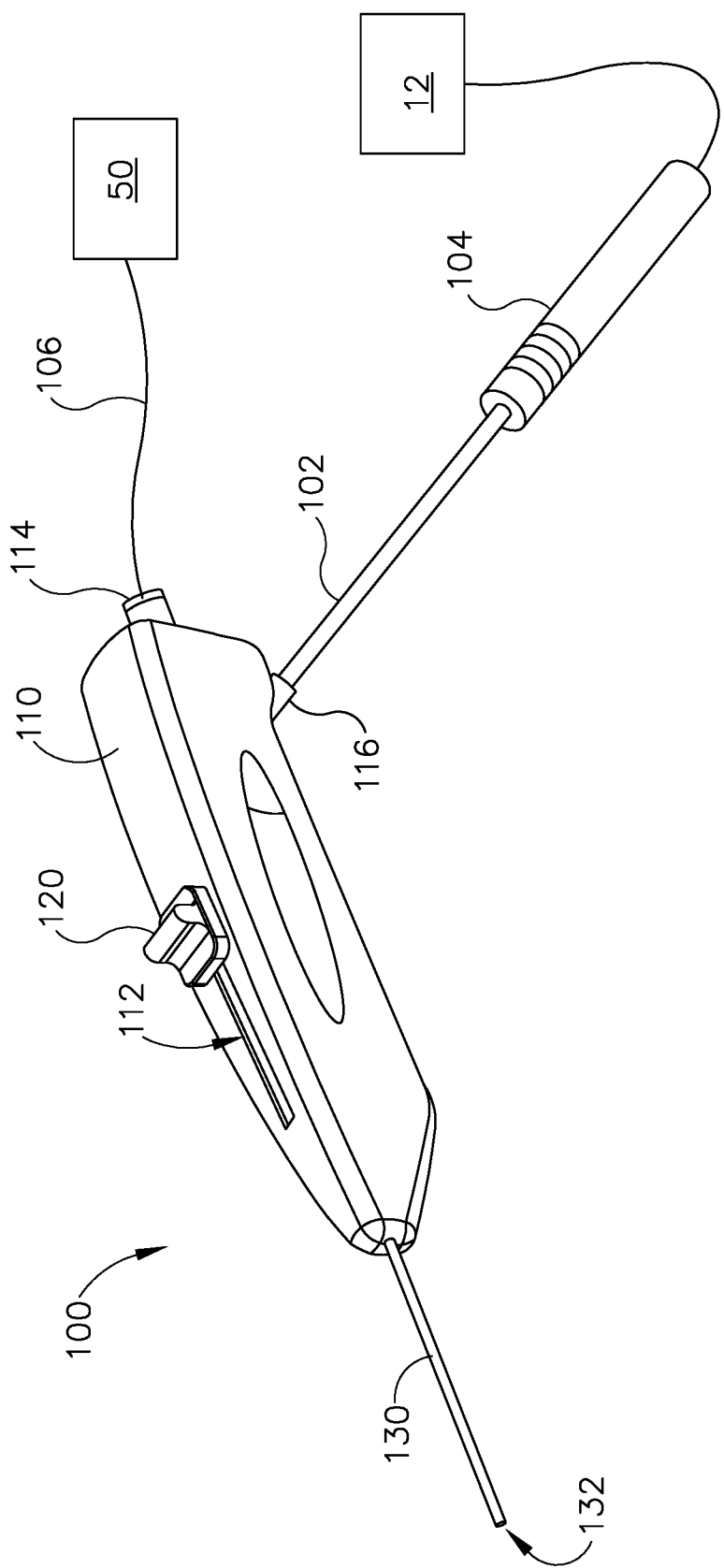
FIG. 2 depicts a perspective view of an exemplary dilation instrument.
Figure 3A:
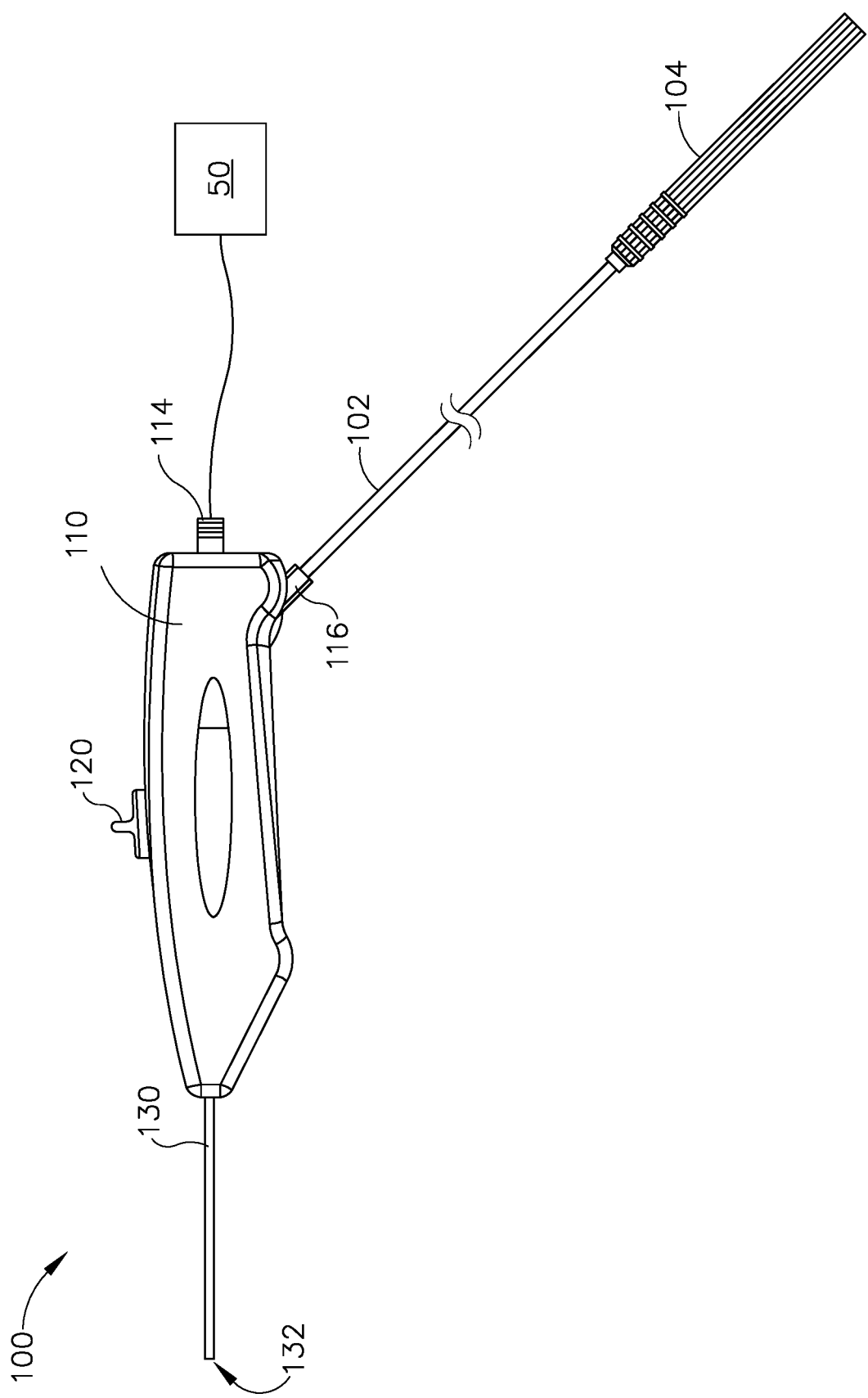
FIG. 3A depicts a side elevational view of the dilation instrument of FIG. 2, with a dilation catheter in a retracted position.
Figure 3B:
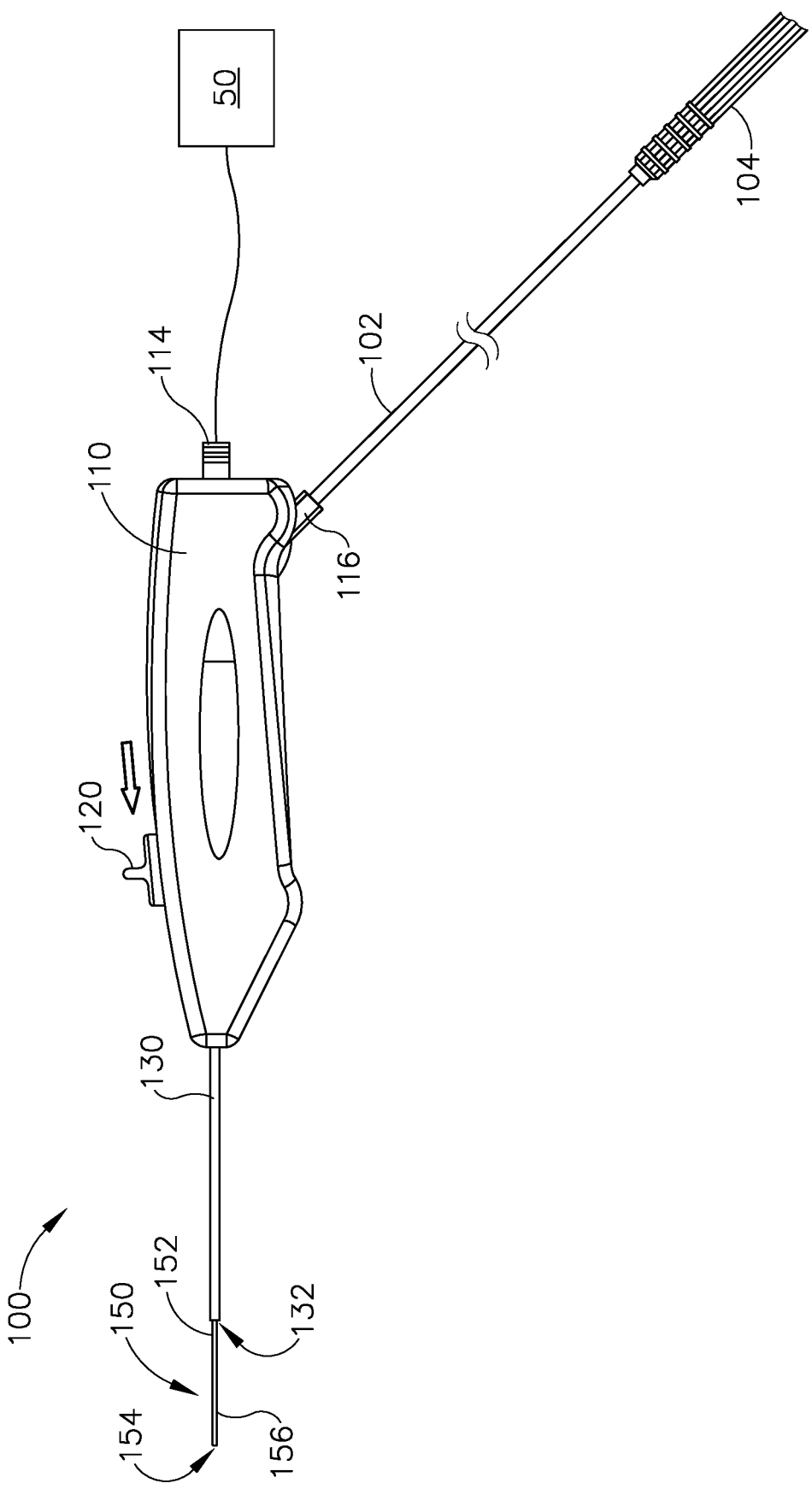
FIG. 3B depicts a side elevational view of the dilation instrument of FIG. 2, with a dilation catheter in an advanced position, and with a dilator of the dilation catheter in a non-expanded state.
Figure 3C:
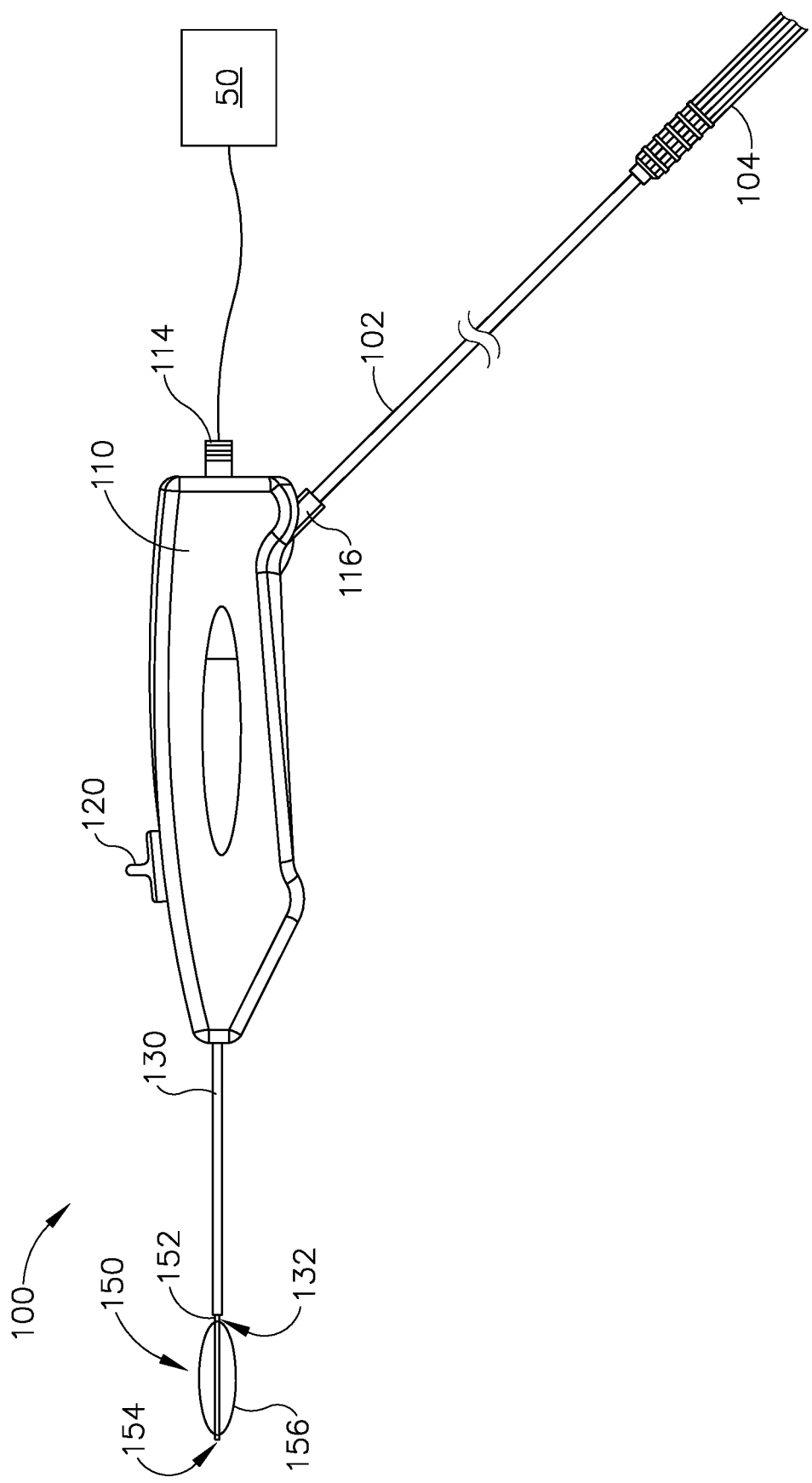
FIG. 3C depicts a side elevational view of the dilation instrument of FIG. 2, with the dilation catheter in the advanced position, and with the dilator in an expanded state.

FIGS. 2-3C show an exemplary dilation instrument (100) that includes a handle assembly (110), a guide tube (130) extending distally from handle assembly (110), and a dilation catheter (150) that is slidably disposed in guide tube (130). Dilation catheter (150) is coupled with a slider (120) of handle assembly (110). Slider (120) is operable to translate longitudinally along a slot (112) of handle assembly (110) to thereby drive dilation catheter (150) between a proximal position (FIG. 3A) and a distal position (FIGS. 3B-3C). Various suitable ways in which slider (120) and dilation catheter (150) may be coupled will be apparent to those skilled in the art in view of the teachings herein.

Handle assembly (110) of the present example further includes an inflation port (114). Inflation port (114) may comprise a conventional luer fitting or any other suitable kind of structure. Inflation port (114) is in fluid communication with a dilator (156) of dilation catheter (150). Dilator (156) will be described in greater detail below. Various suitable ways in which inflation port (114) may be coupled with dilator (156) will be apparent to those skilled in the art in view of the teachings herein. Inflation port (114) is further configured to couple with a conduit (106), which is further coupled with a fluid source (50). Fluid source (50) is configured to provide inflation fluid (e.g., saline, etc.) to dilator (156) via conduit (106) and inflation port (114). By way of example only, fluid source (50) may be configured and operable in accordance with at least some of the teachings of U.S. Pat. No. 9,962,530, entitled "Inflator for Dilation of Anatomical Passageway," issued May 8, 2018, the disclosure of which is incorporated by reference herein.

Handle assembly (110) of the present example further includes a cable port (116), which is coupled with a cable (102). Cable port (116) is further in communication with a position sensor (158) of dilation catheter (150). Position sensor (158) will be described in greater detail below. Various suitable ways in which cable port (116) may be coupled with position sensor (158) will be apparent to those skilled in the art in view of the teachings herein. Cable (102)

leads to a plug (104), which is configured to couple with processor (12) of IGS navigation system (10). Cable port (116), cable (102), and plug (104) thus provide a pathway for communication of position-indicative signals from position sensor (158) to processor (12), thereby enabling processor (12) to determine the position of sensor (158) in three-dimensional space. By way of example only, plug (104) may couple with processor (12) via a conventional USB coupling or in any other suitable fashion. As another merely illustrative example, instrument (100) may provide wireless communication of position-indicative signals from position sensor (158) to processor (12).

Figure 4A:
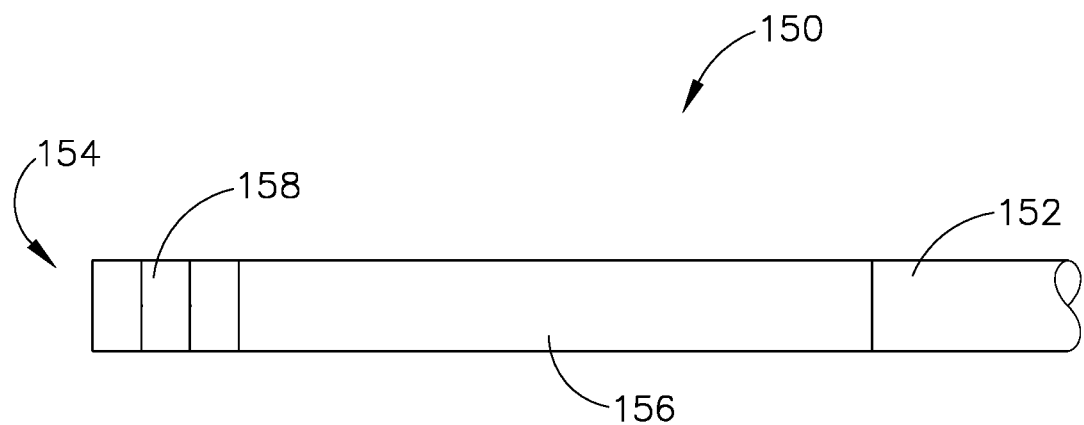
FIG. 4A depicts an enlarged side elevational view of a distal portion of the dilation catheter of FIG. 3A, with the dilator in the non-expanded state.
Figure 4B:
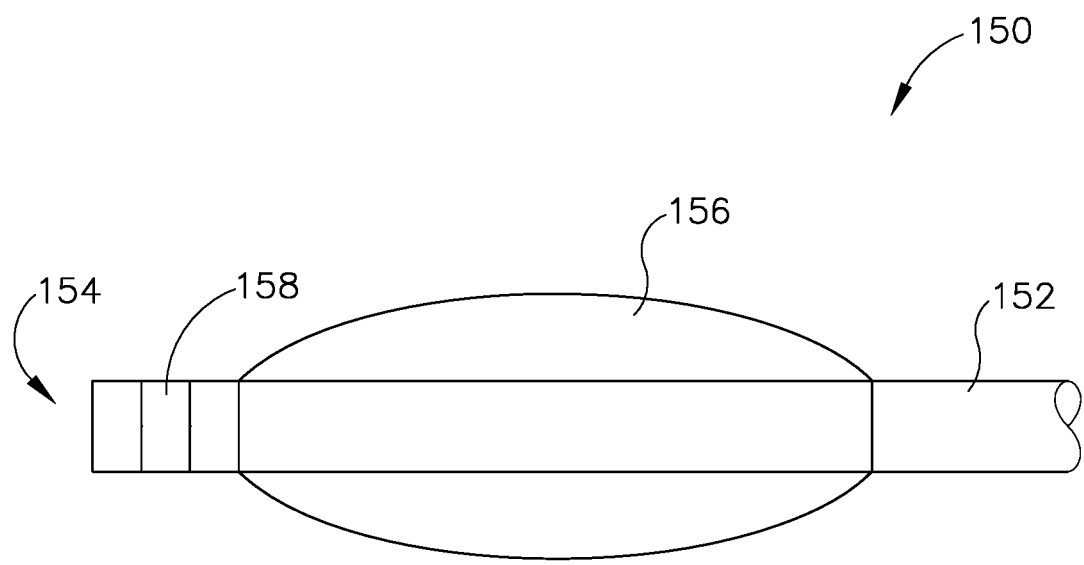
FIG. 4B depicts an enlarged side elevational view of the distal portion of the dilation catheter of FIG. 4A, with the dilator in the expanded state.

As best seen in FIGS. 4A-4B, dilation catheter (150) of the present example includes a shaft (152) with a distal end (154), a dilator (156) that is proximal to distal end (154), and a position sensor (158) that is longitudinally interposed between dilator (156) and distal end (154). Dilator (156) of the present example comprises a balloon that is configured to transition between the non-expanded state (FIG. 4A) and the expanded state (FIG. 4B) based on communication of fluid from and to fluid source (50). In the non-expanded state, dilator (156) is configured to fit within anatomical passageways such as a Eustachian tube, an ostium of a paranasal sinus, and other passageways associated with drainage of a paranasal sinus. In the expanded state, dilator (156) is configured to dilate such a passageway.

Position sensor (158) of the present example comprises a wire coil that is wrapped about the central longitudinal axis of catheter shaft (152). When position sensor (158) is positioned within an alternating electromagnetic field generated by field generators (24), the alternating magnetic field may generate electrical current in position sensor (158), and this electrical current may be communicated along an electrical conduit dilation catheter (150) and further to processor (12) via cable port (116), cable (102), and plug (104). This phenomenon may enable IGS navigation system (10) to determine the location of distal end (154) of dilation catheter (150) within a three-dimensional space (i.e., within the head (H) of the patient (P), etc.). To accomplish this, processor (12) executes an algorithm to calculate location coordinates of the distal end (154) of dilation catheter (150) from the position related signals of the position sensor (158) in dilation catheter (150).

In the present example, when dilation catheter (150) is in the retracted position as shown in FIG. 3A, distal end (154) of dilation catheter (150) is at substantially the same longitudinal position as distal end (132) of guide tube (130). Thus, the signals from position sensor (158) will effectively convey the position of distal end (132) of guide tube (130) when dilation catheter (150) is in the retracted position as shown in FIG. 3A, even if guide tube (130) is in a bent state as described in greater detail below. The operator may thus rely on feedback from IGS navigation system (10) when navigating distal end (132) of guide tube (130) to the appropriate position in the head (H) of the patient (P) while dilation catheter (150) is in the retracted position.

Once distal end (132) of guide tube (130) has reached the appropriate position in the head (H) of the patient (P), and the operator has observed this positioning via IGS navigation system (10), the operator may advance slider (120) along slot (122) to advance dilation catheter (150) relative to guide tube (130) to the advanced position shown in FIG. 3B. Since position sensor (158) is integral with dilation catheter (150), position sensor (158) will also be advanced, thereby providing a signal indicating the location of distal end (154) in the head (H) of the patient (P). The operator may again consult IGS navigation system (10) to observe whether distal end (154) of dilation catheter (150) is at an appropriate position in the head (H) of the patient (P), which may further indicate that dilator (156) is properly located in the targeted anatomical passageway. Once distal end (154) of dilation catheter (154) has reached the appropriate position in the head (H) of the patient (P), and the operator has observed this positioning via IGS navigation system (10), the operator may actuate fluid source (50) to inflate dilator (156) as shown in FIG. 3C and thereby dilate the targeted anatomical passageway.

Figure 5:
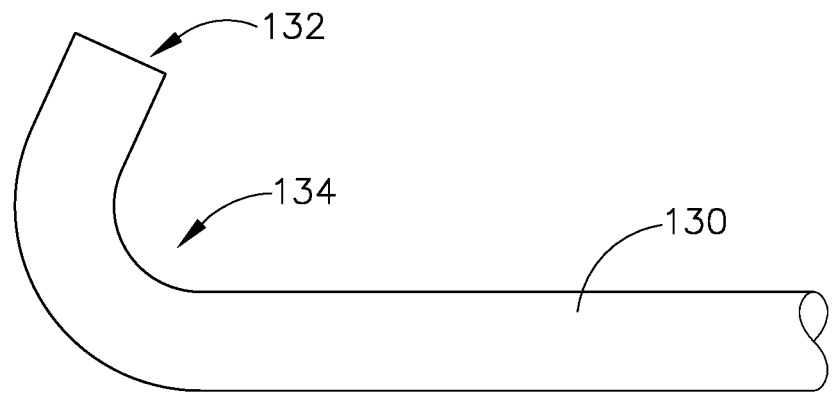
FIG. 5 depicts an enlarged side elevational view of a distal portion of a guide tube of the dilation instrument of FIG. 2 in a bent state.

Guide tube (130) of the present example is formed of a malleable material such as metal. The operator may thus bend guide tube (130) from the straight configuration shown in FIGS. 1-3C to a bent configuration on an ad hoc basis in order to facilitate access to the targeted anatomical passageway. By way of example only, guide tube (130) may be formed of a stainless steel hypotube. FIG. 5 shows an exemplary bent form of guide tube (130), where a bend (134) has been provided just proximal to distal end (132). Various suitable bend angles associated with various potentially targeted anatomical passageways will be apparent to those skilled in the art in view of the teachings herein. Guide tube (130) is configured to maintain bend (134) during normal use of instrument (100), including when dilation catheter (150) translates relative to guide tube (130).

In some scenarios, a separate bending instrument may be used to precisely and reliably form bend (134). An example of such an instrument is described in U.S. Pub. No. 2017/0120020, entitled "Apparatus for Bending Malleable Guide of Surgical Instrument," published May 4, 2017, issued as U.S. Pat. No. 10,137,286 on Nov. 27, 2018, the disclosure of which is incorporated by reference herein. As noted above, since position sensor (158) is effectively positioned at distal end (132) of guide tube (130) when dilation catheter (150) is in the retracted position, signals from position sensor (158) will effectively indicate the position of distal end (132) in three-dimensional space when dilation catheter (150) is in the retracted position.

Figure 6:
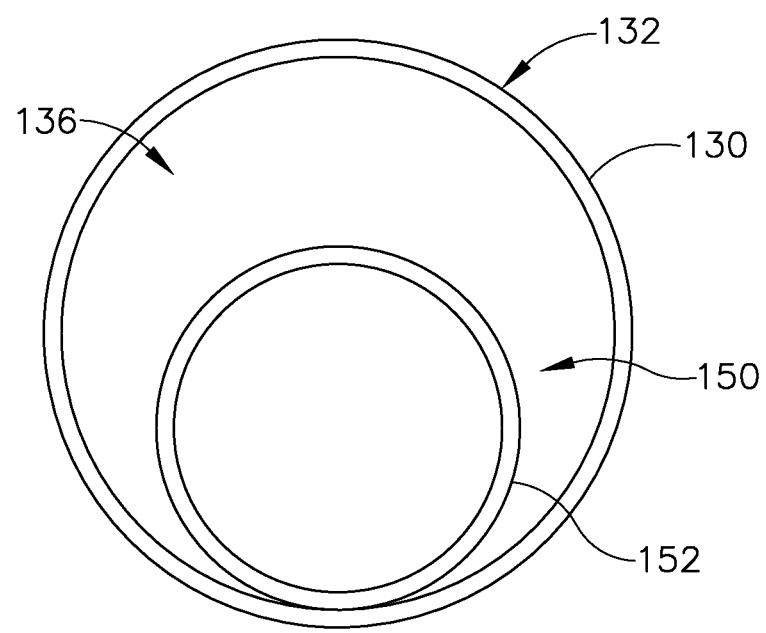
FIG. 6 depicts an end view of the distal end of the dilation catheter of FIG. 3A disposed in the guide tube of FIG. 5.

In some versions, guide tube (130) defines an inner diameter that is substantially larger than the outer diameter of dilation catheter (150), such that a substantial gap is defined between the outer diameter of dilation catheter (150) and the inner diameter of guide tube (130). This may allow instrument (10) to provide suction, irrigation, or other functionality through the gap. Moreover, some such versions may have dilation catheter (150) positioned such that the central longitudinal axis of dilation catheter (150) is laterally offset from the central longitudinal axis of guide tube (130). In other words, by positioning dilation catheter (150) non-coaxially relative to guide tube (130), the gap defined between the outer diameter of dilation catheter (150) and the inner diameter of guide tube (130) may be more easily used to position other features. FIG. 6 shows an example of such an arrangement, where dilation catheter (150) is non-coaxially positioned relative to guide tube (130), and with a substantial gap (136) defined between the outer diameter of dilation catheter (150) and the inner diameter of guide tube (130) may be more easily used to position other features. By way of example only, an irrigation device, suction device, ablation device, or other device may be positioned in gap (136).

III. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a handle assembly; (b) a guide tube extending distally from the handle assembly, wherein at least a distal portion of the guide tube is malleable; and (c) a dilation catheter slidably positioned in the guide tube, wherein the dilation catheter includes: (i) a distal end, (ii) a dilator, and (iii) a position sensor, wherein the position sensor is configured to generate a signal indicating a position of the position sensor in three-dimensional space, wherein the dilation catheter is configured to translate relative to the guide tube.

Example 2

The apparatus of Example 1, wherein the handle assembly includes an inflation port, wherein the inflation port is configured to couple the dilator with an external fluid source.

Example 3

The apparatus of Example 2, further comprising a fluid source in fluid communication with the inflation port, wherein the dilator is configured to receive fluid from the fluid source to thereby transition from a non-expanded state to an expanded state.

Example 4

The apparatus of any one or more of Examples 1 through 3, wherein the handle assembly further includes a data port, wherein the data port is configured to couple the position sensor with an external image guided surgery system.

Example 5

The apparatus of Example 4, wherein the data port comprises a cable port, wherein the data port is configured to couple the position sensor with an external image guided surgery system via a cable.

Example 6

The apparatus of any one or more of Examples 1 through 5, the handle assembly further comprising a slider coupled with the dilation catheter, wherein the slider is operable to drive the dilation catheter relative to the handle assembly between a retracted position and an advanced position.

Example 7

The apparatus of Example 6, wherein the dilation catheter has a distal end, wherein the distal end of the dilation catheter is configured to be positioned at or proximal to a distal end of the guide tube when the dilation catheter is in the retracted position.

Example 8

The apparatus of any one or more of Examples 6 through 7, wherein the distal end of the dilation catheter is configured to be positioned distal to a distal end of the guide tube when the dilation catheter is in the advanced position.

Example 9

The apparatus of any one or more of Examples 1 through 8, wherein the guide tube comprises a hypotube.

Example 10

The apparatus of any one or more of Examples 1 through 9, wherein the guide tube defines an inner diameter, wherein the dilation catheter defines an outer diameter, wherein the guide tube and the dilation catheter cooperate to define a gap between the inner diameter of the guide tube and the outer diameter of the dilation catheter.

Example 11

The apparatus of Example 10, wherein the gap is sized to provide communication of one or more of: (i) suction through the gap, (ii) irrigation fluid through the gap, or (iii) another instrument through the gap.

Example 12

The apparatus of any one or more of Examples 10 through 11, wherein the guide tube defines a first central longitudinal axis, wherein the dilation catheter defines a second central longitudinal axis, wherein the second central longitudinal axis is laterally offset from the first central longitudinal axis.

Example 13

The apparatus of any one or more of Examples 1 through 12, wherein the position sensor is longitudinally interposed between the distal end of the dilation catheter and the dilator.

Example 14

The apparatus of any one or more of Examples 1 through 13, wherein the position sensor comprises a wire coil positioned coaxially about a central longitudinal axis of the dilation catheter.

Example 15

The apparatus of any one or more of Examples 1 through 14, wherein the dilator comprises a balloon.

Example 16

An apparatus, comprising: (a) a dilation instrument, the dilation instrument comprising: (i) a guide tube having a malleable distal portion, and (ii) a dilation catheter slidably positioned in the guide tube, wherein the dilation catheter is configured to translate relative to the guide tube, wherein the dilation catheter includes: (A) a distal end, (B) a dilator, and (C) a position sensor; (b) a fluid source in fluid communication with the dilator; and (c) an image guided surgery system in communication with the position sensor, wherein the image guided surgery system is configured to determine a position of the position sensor in three-dimensional space based on signals generated by the position sensor.

Example 17

The apparatus of Example 17, wherein the image guided surgery system is further configured to determine a position of a distal end of the guide tube in three-dimensional space based on signals generated by the position sensor when the dilation catheter is in a retracted position relative to the guide tube.

Example 18

The apparatus of any one or more of Examples 16 through 17, further comprising a handle, wherein the guide tube extends distally from the handle.

Example 19

The apparatus of Example 18, wherein the fluid source is remote from the handle, wherein the handle is coupled with the fluid source via a conduit.

Example 20

An apparatus comprising: (a) a handle assembly, the handle assembly including: (i) a slider, (ii) a fluid port, and (iii) a data port; (b) a guide tube extending distally from the handle assembly, wherein at least a distal portion of the guide tube is malleable; and (c) a dilation catheter slidably positioned in the guide tube, wherein the dilation catheter is coupled with the slider, wherein the slider is operable to translate the dilation catheter relative to the guide tube, wherein the dilation catheter includes: (i) a distal end, (ii) a dilator in fluid communication with the fluid port, and (iii) a position sensor in communication with the data port, wherein the position sensor is configured to generate a signal indicating a position of the position sensor in three-dimensional space.

IV. MISCELLANEOUS

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one skilled in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. An apparatus comprising:
(a) a handle assembly including:
(i) an inflation port,
(ii) a data port, the data port comprising a cable port, and
(iii) a slider;
(b) a guide tube extending distally from the handle assembly, the guide tube having a distal end, at least a distal portion of the guide tube comprising a malleable stainless steel hypotube, the guide tube defining a first central longitudinal axis; and
(c) a dilation catheter coupled with the slider and slidably positioned in the guide tube, the dilation catheter defining a second central longitudinal axis, the second central longitudinal axis being laterally offset from the first central longitudinal axis of the guide tube, the slider being operable to drive the dilation catheter longitudinally relative to the handle assembly between a retracted position and an advanced position, the dilation catheter including:
(i) a distal end configured to be positioned at or proximal to the distal end of the guide tube when the dilation catheter is in the retracted position, the distal end of the dilation catheter being further configured to be positioned distal to the distal end of the guide tube when the dilation catheter is in the advanced position,
(ii) a dilator comprising a balloon, the inflation port being configured to couple the dilator with an external fluid source, and
(iii) a position sensor, the position sensor being configured to generate a signal indicating a position of the position sensor in three-dimensional space, the position sensor being longitudinally interposed between the distal end of the dilation catheter and the dilator, the position sensor comprising a wire coil positioned coaxially about the second central longitudinal axis, the data port being further configured to couple the position sensor with an external image guided surgery system via a cable coupled with the cable port,
the dilation catheter being configured to translate relative to the guide tube,
the guide tube defining an inner diameter, the dilation catheter defining an outer diameter, the guide tube and the dilation catheter cooperating to define a gap between the inner diameter of the guide tube and the outer diameter of the dilation catheter, and
the gap being sized to provide:
(A) a fluid path for an irrigation device through the gap,
(B) a fluid path for a suction device through the gap, and
(C) advancement of a guidewire along the gap, the gap being sized to provide advancement of the guidewire along the gap, the guidewire being positioned lateral to the dilation catheter.
2. The apparatus of claim 1, further comprising a fluid source in fluid communication with the inflation port, the dilator being configured to receive fluid from the fluid source to thereby transition from a non-expanded state to an expanded state.
3. The apparatus of claim 1, a proximal portion of the guide tube comprising the malleable stainless steel hypotube, the malleable stainless steel hypotube extending to the handle, the distal portion of the guide tube being configured to be bent by a separate bending instrument and to thereafter maintain a bend.

4. An apparatus comprising:
(a) a handle assembly including a slot, the handle assembly including:
(i) a slider configured to longitudinally advance along the slot,
(ii) a fluid port, and
(iii) a data port;
(b) a guide tube extending distally from the handle assembly, at least a distal portion of the guide tube being malleable stainless steel, the guide tube including an inner surface defining an inner diameter, the guide tube further defining a central longitudinal axis; and
(c) a dilation catheter slidably positioned in the guide tube, the dilation catheter being coupled with the slider, the slider being operable to translate the dilation catheter relative to the guide tube, the dilation catheter including:
(i) a distal end configured to be positioned at or proximal to a distal end of the guide tube when the dilation catheter is in a retracted position and further configured to be positioned distal to the distal end of the guide tube when the dilation catheter is in an advanced position,
(ii) a dilator in fluid communication with the fluid port, the dilator being configured to transition between a non-expanded state and an expanded state, the dilator being sized to fit within a Eustachian tube when in the non-expanded state and is sized to dilate the Eustachian tube when in the expanded state,
(iii) a position sensor in communication with the data port, the position sensor being configured to generate a signal indicating a position of the position sensor in three-dimensional space, the position sensor being longitudinally interposed between the dilator and the distal end of the dilation catheter, and
(iv) a shaft, the shaft defining a central longitudinal axis, the central longitudinal axis of the shaft being laterally offset from the central longitudinal axis of the guide tube, a first portion of the shaft being positioned to contact the inner surface of the guide tube, a second portion of the shaft defining a gap between an outer surface of the second portion of the shaft and the inner surface of the guide tube;
the gap being sized to provide:
(A) a fluid path for irrigation fluid through the gap,
(B) a fluid path for suction through the gap, and
(C) advancement of another instrument along the gap,
the distal portion of the guide tube being configured to maintain a first bend such that each of the dilator, fluid path for irrigation, fluid path for suction, and the other instrument achieves a first exit angle, the distal portion of the guide tube being further configured to transition from the first bend to a second bend such that each of the dilator, fluid path for irrigation, fluid path for suction, and the other instrument achieves a second exit angle, each of the first and second bends being angularly offset from the central longitudinal axis of the guide tube, the distal portion of the guide tube being configured to maintain each of the first and second bends, the first exit angle being configured for placement of the dilator during dilation of a maxillary sinus ostium, the second exit angle being configured for placement of the dilator during dilation of a frontal sinus.

* * * * *